United States Patent [19]
Aviron-Violet et al.

[11] Patent Number: 4,943,679
[45] Date of Patent: Jul. 24, 1990

[54] PROCESS FOR THE N-ω-TRIFLUOROACETYLATION OF SATURATED ALIPHATIC MONOCARBOXYLIC α,ω-DIAMINO ACIDS

[75] Inventors: Paul Aviron-Violet, Saint-Genis; Christian Gervals, Villeurbanne, both of France

[73] Assignee: Rhone Poulenc Chimie, Courbevoie, France

[21] Appl. No.: 147,531

[22] Filed: Jan. 25, 1988

[30] Foreign Application Priority Data

Jan. 26, 1987 [FR] France ................................ 87 01031

[51] Int. Cl.$^5$ ............................................ C07C 103/48
[52] U.S. Cl. .................................................... 562/561
[58] Field of Search ................................ 562/561, 574

[56] References Cited
FOREIGN PATENT DOCUMENTS 239063 9/1987 European Pat. Off. ............ 562/561

OTHER PUBLICATIONS

Steylich, Synthesis, pp. 399–401 (1976).
Blacklock, Pept. Struct. Funct., Proc. Am. Pept. Symp., 9th, pp. 787–790 (1985).

*Primary Examiner*—Michael Shippen
*Attorney, Agent, or Firm*—Finnegan, Henderson, Farabow, Garrett, and Dunner

[57] ABSTRACT

A process for the N-ω-trifluoroacetylation of a saturated aliphatic monocarboxylic α,ω-diamino acid. A saturated aliphatic monocarboxylic α,ω-diamino acid of the formula:

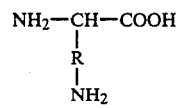

wherein R represents a straight-chain or branched-chain $C_1$–$C_6$ alkylene radical, is contacted with a $C_1$–$C_6$ straight-chain or branched-chain alkyl trifluoroacetate.

16 Claims, No Drawings

PROCESS FOR THE N-ω-TRIFLUOROACETYLATION OF SATURATED ALIPHATIC MONOCARBOXYLIC α,ω-DIAMINO ACIDS

FIELD OF THE INVENTION

The present invention relates to a process for the N-ω-trifluoroacetylation of saturated aliphatic monocarboxylic α,ω-diamino acids

BACKGROUND OF THE INVENTION

The trifluoroacetylation of basic amino acids, such as lysine or ornithine, among others, using trifluoroacetic anhydride in an acid medium is known (Weygand et al., Chem. Ber. 89, 647 (1956)). It has been observed in such prior art processes that the trifluoroacetylation reaction of amino acids containing two amine groups preferentially takes place on the amine group in the α-position relative to the carboxyl group, or simultaneously on the two amine groups.

The trifluoroacetylation of the amine group at the end of the chain of amino acids such as lysine and ornithine, by reacting such acids with ethyl thioltrifluoroacetate in an aqueous basic medium, has been proposed (Schallenberg et al., Journal of American Chem. Soc. 77,2779, (1955)). Ethyl thioltrifluoroacetate, however, is a material which is expensive, polluting, and unavoidably gives an odor of sulfur to the amino acid prepared. Additionally, although Schallenberg et al. indicates that N-ω-trifluoroacetylation occurs, it has been found that this process does not enable saturated aliphatic monocarboxylic α,ω-diamino acids to be N-trifluoroacetylated in the ω-position with an adequate selectivity. Indeed, it has been found that the process of Schallenberg et al. does not prevent α-trifluoroacetylated and α,ω-ditrifluoroacetylated derivatives from being formed in significant amounts.

T. J. Curphey (J. Org. Chem., 44 (15) 2805 (1979)) has described the N-trifluoroacetylation of α-amino acids containing a single —NH₂ amine group, using ethyl trifluoroacetate in the presence of a triethylamine-type base and anhydrous methanol, over a period of at least fourteen hours The products obtained are N-α-trifluoroacetylated. The instant inventors have observed that saturated aliphatic monocarboxylic α,ω-diamino acids are not N-trifluoroacetylated regioselectively at the ω-position when treated by the Curphey process.

SUMMARY OF THE INVENTION

The present inventors have found a process which enables saturated aliphatic monocarboxylic α,ω-diamino acids to be N-trifluoroacetylated regioselectively at the ω-position.

The present invention relates to a process for the N-ω-trifluoroacetylation of saturated aliphatic monocarboxylic α,ω-diamino acids using a $C_1$-$C_4$, preferably a $C_1$-$C_2$, straight-chain or branched-chain alkyl trifluoroacetate.

DETAILED DESCRIPTION OF THE INVENTION

The saturated aliphatic monocarboxylic α,ω-diamino acids employed are racemates or are optically active and may be represented by the following formula:

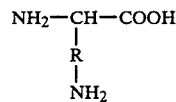

in which R represents a straight-chain or branched-chain $C_1$-$C_6$ alkylene radical.

These compounds may advantageously be lysine or ornithine.

The N-ω-trifluoroacetylation operation may be carried out using 1 to 2 moles, preferably 1 to 1.50 moles, most preferably 1 to 1.25 moles, of alkyl trifluoroacetate per mole of saturated aliphatic monocarboxylic α,ω-diamino acid This operation may be carried out in the presence of a diluting agent comprising a $C_1$-$C_5$, preferably $C_1$-$C_4$, straight-chain or branched-chain alkanol and/or an excess of alkyl trifluoroacetate.

Said alkanol may be employed in the pure form or, alternatively, it may contain up to 10%, preferably 5%, of its volume of water. Said excess of alkyl trifluoroacetate may also contain up to 10% of its volume of water; however, it is preferable to use it in the pure form.

The quantity of diluting agent employed may range from 0.5 to 10 liters, preferably from 0.5 to 2 liters, per mole of saturated aliphatic monocarboxylic α,ω-diamino acid, so as to obtain a medium which is easy to stir.

Among alkanols which may be employed, there may be mentioned methanol, ethanol, isopropanol and tert-butanol.

The N-ω-trifluoroacetylation operation may advantageously be carried out at atmospheric pressure at temperatures on the order of 0° to 50° C., preferably from 20° to 25° C.

The duration of the N-ω-trifluoroacetylation reaction is generally on the order of 15 minutes to 15 hours, preferably from 15 minutes to 3 hours, most preferably from 2 to 3 hours.

The N-ω-trifluoroacetylated product obtained may then be separated from the reaction medium (for example, by any physical separation process, such as filtration) and it may then be purified by any known means (for example, by recrystallization in a water-alcohol mixture.) These operations may be repeated several times, if desired.

The process which forms the subject of the invention has the advantage of not requiring the presence of any reagent other than the saturated aliphatic monocarboxylic α,ω-diamino acid and the alkyl trifluoroacetate. In particular, the presence of a base (for example, a trialkylamine), is not required. Trialkylamines even have the tendency of being deleterious in obtaining satisfactory progress of the N-ω-trifluoroacetylation reaction.

This process enables N-ω-trifluoroacetylated derivatives of saturated aliphatic monocarboxylic α,ω-diamino acids to be obtained with a selectivity for the N-ω-trifluoroacetylated derivative which is greater than 90%, relative to the quantity of saturated aliphatic monocarboxylic α,ω-diamino acid converted.

The N-ω-trifluoroacetylated derivatives obtained according to the process of the invention may be employed especially for the preparation of carboxyalkylated dipeptides, for example, according to the process described in European Patent Application No. 168,769.

The following examples illustrate certain embodiments of the invention and should not be regarded as limiting the scope or spirit of the invention.

EXAMPLE 1

1.61 moles (235 g) of L-lysine and 1.61 liters of ethanol were charged into a 3 liter reactor.

This mixture was stirred using a bar magnet, and 2.02 moles (287 g) of ethyl trifluoroacetate were added thereto over half an hour.

The mixture was stirred for one and a half hours.

337 g of a precipitate were recovered by filtration, which precipitate was dried.

This precipitate was analyzed by high performance liquid chromatography. The following titers were observed:

88% by weight of lysine N-ω-trifluoroacetate and

12% by weight of unconverted lysine (only traces of lysine α-trifluoroacetate and lysine α,ω-ditrifluoroacetate were found), which corresponds to a crude lysine ω-trifluoroacetate yield of 76%.

280 g of this precipitate were recrystallized in 3.76 liters of ethanol under reflux, to which 1.12 liters of water were added in small amounts until they were completely dissolved.

Lysine ω-trifluoroacetate precipitated on cooling, the lysine remaining in the aqueous solution.

The lysine ω-trifluoroacetate precipitated was filtered and then dried.

170 g of lysine ω-trifluoroacetate, having a titer in the region of 100% and having a specific rotation as follows, were then recovered: $\alpha_D^{20} = +20.6°$ (c=3, dichloroacetic acid) [the theoretical specific rotation for this substance is: $\alpha_D^{20} = +20.5°$], which corresponds to a crystallized lysine ω-trifluoroacetate yield of 52.5%.

On concentrating the filtrate and recrystallization, a further amount of 52 g of lysine ω-trifluoroacetate were recovered.

An overall recrystallized lysine N-ω-trifluoroacetate yield of 68.5%, relative to the starting lysine, was therefore obtained.

The structure of lysine ω-trifluoroacetate is confirmed by mass spectrometry or NMR spectrometry.

EXAMPLE 2

The experiment described in Example No. 1 was repeated in this example, but replacing the 1.61 liters of ethanol with the same volume of ethyl trifluoroacetate.

The precipitate obtained at the end of the stirring period (one and a half hours) was washed with ethanol until all traces of ethyl trifluoroacetate were removed. The following crude product yields were obtained:
lysine ω-trifluoroacetate: 90%
lysine α-trifluoroacetate: 1%
lysine α,ω-ditrifluoroacetate: traces The relative selectivity for lysine ω-trifluoroacetate was 98.9%.

EXAMPLES 3 TO 16

These examples were accomplished according to the procedure in Example 1.

The nature of the compounds employed, their quantity and the operating conditions are given in Table I.

The yields of crude lysine ω-trifluoroacetate, crude lysine α,ω-ditrifluoroacetate and crude lysine α-trifluoroacetate, which are also given in Table I, show that the selectivity for lysine ω-trifluoroacetate was greater than 90%.

EXAMPLE 17

The experiment described in Example 14 was repeated in this example, but the 6.25 mmoles of ethyl trifluoroacetate were replaced with 5 mmoles of methyl trifluoroacetate.

At the end of the stirring period (2 hours), the following crude product yields were obtained:
lysine ω-trifluoroacetate: 79%
lysine α-trifluoroacetate: 1.5%
lysine α,ω-ditrifluoroacetate: traces The relative selectivity for lysine ω-trifluoroacetate was 98%.

EXAMPLES 18 TO 21

These examples, which are given by way of comparison, were accomplished according to the procedure in Examples 3 to 16, but in the presence of a base according to the process described by Curphey (J. Org. Chem., 44, (15), 2805 (1979)).

The nature of the compounds employed, their quantity and the operating conditions are given in Table II.

It is observed that the selectivity for lysine ω-trifluoroacetate is well below 90%.

EXAMPLES 22 TO 25

These examples are given by way of comparison.

The trifluoroacetylating agent in these examples was ethyl thioltrifluoroacetate, employed under the conditions described by Schallenberg et al. (Journal of American Chem. Soc. 77, 2779 (1955)).

These examples were accomplished as follows:

10.3 mmoles of lysine were charged into a 50 ml reactor. 21 ml of 0.5N NaOH (which dissolved the lysine in a few minutes) were introduced, with stirring. The pH was then between 10.6 and 11. The pH was then adjusted at ambient temperature to the desired value with 9N or 3N sulfuric acid. The ethyl thioltrifluoroacetate was then added over 20 minutes, and the pH was then adjusted by adding 1N sodium hydroxide.

The results obtained at different pH values are given in Table III.

The selectivity for lysine ω-trifluoroacetate was always significantly below 90%.

EXAMPLE 26

(According to the Invention, with Recycling)

(A) Reaction of lysine with ethyl trifluoroacetate

A 250 ml Erlenmeyer flask was charged with:
7.3 grams of lysine
50 ml of ethanol
8.87 grams of ethyl trifluoroacetate The 8.87 grams of ethyl trifluoroacetate were added into the other ingredients over 2 minutes at ambient temperature. The reaction mixture was stirred for two hours at ambient temperature, and then filtered. The precipitate was then washed twice with 25 ml of ethanol, followed by drying the precipitate (the volume of filtrate equaled 104 ml.).

11.39 grams of powder (a yield of 93%) were obtained containing 14.8% of non-transformed lysine. The conversion of the lysine was 77%.

(B) Separation of ω-TFA lysine from the non-transformed lysine 11 grams of the powder containing 14.8% non-transformed lysine and 147 ml of ethanol were mixed at 78° C. 42 ml of distilled water were added to the mixture over 1 hour and 40 minutes.

The mixture was then refrigerated and maintained for two hours at 3° C.

The solids were then filtered, and washed twice with 30 ml of ethanol and dried. 6.5 grams of solids (containing 0.9% lysine) were obtained. The volume of the filtrate was 252 ml and contained 1.6 grams of lysine. The filtrate was evaporated, and 4.1 grams of powder containing about 39% lysine were recovered.

(C) Recycling

The 4.1 grams of powder containing about 39% lysine (corresponding to about 1.6 grams of lysine) were put in solution with 5.7 grams of supplementary lysine in 50 ml of ethanol. 8.87 grams of ethyl trifluoroacetate were added, and reacted for two hours at ambient temperature.

The precipitate which was obtained was filtered, washed two times with 25 ml of ethanol, and dried. 13.2 grams of powder containing 14.3% of lysine were obtained. (The conversion of the lysine equaled 74%).

(D) Separation of the ω-TFA lysine from the non-transformed lysine 13 grams of the powder containing 14.3% lysine (1.86 grams of lysine), 147 ml of ethanol and 54 ml of distilled water were mixed.

The procedure of step (B) was followed. 7.7 grams of solids were obtained containing: 1.8% of lysine and 97% of ω-TFA lysine.

TABLE I

| Ex. | Lysine (mmole) | Et TFA (mmole) | Alkanol nature | ml | t °C. | time (hours) | Crude (lys)-TFA yields % ω | α,ω | α | Relative selectivity for (lys) ω-TFA % |
|---|---|---|---|---|---|---|---|---|---|---|
| 3 | 5 | 5 | Et OH | 5 | 25 | 2 | 40 | traces | traces | 100 |
| 4 | 5 | 6.25 | Et OH | 5 | 25 | 2 | 84 | traces | traces | 100 |
| 5 | 5 | 7.5 | Et OH | 5 | 25 | 2 | 85 | traces | traces | 100 |
| 6 | 5 | 6.25 | Et OH | 5 | 25 | ¼ | 63 | traces | traces | 100 |
| 7 | 5 | 6.25 | Et OH | 5 | 25 | ½ | 76 | traces | traces | 100 |
| 8 | 5 | 6.25 | Et OH | 5 | 25 | 1 | 74 | traces | traces | 100 |
| 9 | 5 | 6.25 | Et OH | 5 | 25 | 3 | 76 | traces | traces | 100 |
| 10 | 5 | 6.25 | Et OH | 5 | 50 | 2 | 32 | traces | traces | 100 |
| 11 | 5 | 6.25 | Et OH | 10 | 25 | 2 | 80 | traces | traces | 100 |
| 12 | 5 | 6.25 | Me OH | 2.5 | 25 | 3 | 76 | traces | traces | 100 |
| 13 | 5 | 6.25 | Me OH | 3.5 | 25 | 3 | 80 | traces | traces | 100 |
| 14 | 5 | 6.25 | Me OH | 5 | 25 | 2 | 78 | 3.5 | traces | 95.7 |
| 15 | 5 | 6.25 | Isopropanol | 5 | 25 | 1 H ¾ | 84 | traces | traces | 100 |
| 16 | 5 | 6.25 | Tert-butanol | 5 | 25 | 1 H ¾ | 68 | traces | traces | 100 |

Et TFA: ethyl trifluoroacetate
(lys) ω-TFA: lysine ω-trifluoroacetate
(lys) α,ω-TFA: lysine α,ω-ditrifluoroacetate
(lys) α-TFA: lysine ω-trifluoroacetate
Et OH: ethanol
Me OH: methanol

TABLE II

| Ex. | Lysine (mmole) | Et TFA (mmole) | Alkanol nature | ml | Triethylamine (mmole) | t °C. | time (hours) | Crude (lys)-TFA yields % ω | α,ω | α | Relative selectivity for (lys)ω-TFA % |
|---|---|---|---|---|---|---|---|---|---|---|---|
| 18 | 5 | 6.25 | Me OH | 2.5 | 5 | 25 | 15 | 58 | 23 | 3 | 69 |
| 19 | 5 | 6.25 | Me OH | 2.5 | 10 | 25 | 15 | 45 | 25 | 4 | 60.8 |
| 20 | 5 | 6.25 | Me OH | 2.5 | 5 | 50 | 15 | 62 | 13.5 | 3 | 79 |
| 21 | 5 | 6.25 | Me OH | 2.5 | 5 | 25 | 3 | 50 | 35 | 10 | 52.6 |

TABLE III

| Ex. | Lysine (mmole) | Et SH TFA (mmole) | pH | t °C. | time (hours) | Relative selectivity for crude (lys)-TFA % ω | α,ω | α |
|---|---|---|---|---|---|---|---|---|
| 22 | 10.3 | 16.4 | 7.5 | 25 | 16 | 55 | 17 | 28 |
| 23 | 10.3 | 16.4 | 8 | 25 | 21 | 43.5 | 25.5 | 31 |
| 24 | 10.3 | 16.4 | 9 | 25 | 17 | 34 | 13 | 5 |
| 25 | 10.3 | 16.4 | 10 | 25 | 1 H 10 | 85.5 | 12 | 2.5 |

Et SH TFA: ethyl thioltrifluoroacetate

We claim:

1. A process for the for the N-ω-trifluoroacetylation of a saturated aliphatic monocarboxylic α,ω-diamino acid, comprising the step of contacting in an alcoholic medium a saturated aliphatic monocarboxylic α,ω-diamino acid of the formula:

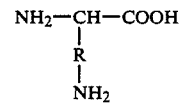

wherein R represents a straight-chain or branched-chain $C_1$–$C_6$ alkylene radical, with a $C_1$–$C_4$ straight-chain or branched-chain alkyl trifluoroacetate in the absence of a base for a time sufficient to N-ω-trifluoroacetylate said α,ω-diamino acid.

2. The process of claim 1, wherein said alkyl trifluoroacetate is a $C_1$–$C_2$ straight-chain or branched-chain alkyl trifluoroacetate.

3. The process of claim 1, wherein said α,ω-diamino acid is lysine or ornithine.

4. The process of claim 1, wherein said N-ω-trifluoroacetylation is carried out using from 1 to 2 moles of alkyl trifluoroacetate per mole of saturated aliphatic monocarboxylic α,ω-diamino acid.

5. The process of claim 4, wherein said N-ω-trifluoroacetylation is carried out using from 1 to 1.50 moles of alkyl trifluoroacetate per mole of saturated aliphatic monocarboxylic α,ω-diamino acid.

6. The process of claim 1, wherein said N-ω-trifluoroacetylation is carried out in the presence of a diluting agent comprising a $C_1$–$C_5$ straight-chain or branched-chain alkanol and/or an excess of said alkyl trifluoroacetate.

7. The process of claim 6, wherein said diluting agent consists of a $C_1$–$C_4$ straight-chain or branched-chain alkanol.

8. The process of claim 7, wherein said diluting agent consists of methanol, ethanol, isopropanol or tert-butanol.

9. The process of claim 6, wherein said diluting agent contains up to 10% of its volume of water.

10. The process of claim 6, wherein the volume of said diluting agent employed ranges from 0.5 to 10 liters per mole of saturated aliphatic monocarboxylic α,ω-diamino acid.

11. The process of claim 10, wherein the volume of said diluting agent employed ranges from 0.5 to 2 liters per mole of saturated aliphatic monocarboxylic α,ω-diamino acid.

12. The process of claim 1, wherein the N-ω-trifluoroacetylation is carried out at atmospheric pressure and at a temperature ranging from 0° to 50° C.

13. The process of claim 12, wherein said N-ω-trifluoroacetylation is carried out at a temperature ranging from 20° to 25° C.

14. The process of claim 1, wherein the N-ω-trifluoroacetylation is carried out with stirring for a time ranging from 15 minutes to 15 hours.

15. The process of claim 14, wherein said N-ω-trifluoroacetylation is carried out over 2 to 3 hours.

16. A process for the preparation of lysine N-ω-trifluoroacetate by an N-ω-trifluoroacetylation reaction comprising the step of contacting lysine with either ethyl trifluoroacetate or methyl trifluoroacetate in the presence of ethanol as a diluting agent and in the absence of a base for a time sufficient to N-ω-trifluoroacetylate said lysine.

* * * * *